United States Patent
Solèr et al.

(10) Patent No.: US 7,827,694 B2
(45) Date of Patent: Nov. 9, 2010

(54) METHOD FOR MANUFACTURING ONE-PIECE DENTAL DEVICE

(75) Inventors: Christoph Solèr, Zwingen (CH); Ulrich Mundwiler, Tenniken (CH); Marco Wieland, Basel (CH)

(73) Assignee: Straumann Holding AG, Basel (CH)

( * ) Notice: Subject to any disclaimer, the term of this patent is extended or adjusted under 35 U.S.C. 154(b) by 97 days.

(21) Appl. No.: 11/132,990

(22) Filed: May 19, 2005

(65) Prior Publication Data
US 2005/0266382 A1 Dec. 1, 2005

(30) Foreign Application Priority Data
May 19, 2004 (EP) ................... 04011868

(51) Int. Cl.
*B21F 43/00* (2006.01)
(52) U.S. Cl. ............... 29/896.1; 433/173; 433/174; 433/201.1; 433/221
(58) Field of Classification Search ................ 433/173, 433/174, 201.1, 221; 29/896.1
See application file for complete search history.

(56) References Cited

U.S. PATENT DOCUMENTS

| | | | |
|---|---|---|---|
| 3,628,248 A * | 12/1971 | Kroder et al. | 433/175 |
| 4,252,525 A * | 2/1981 | Child | 433/173 |
| 4,259,072 A * | 3/1981 | Hirabayashi et al. | 433/173 |
| 5,026,280 A | 6/1991 | Duerr et al. | |
| 5,052,931 A | 10/1991 | Kirsch | |
| 5,492,470 A * | 2/1996 | Anders | 433/169 |
| 5,509,804 A | 4/1996 | Arzt | |
| 5,536,122 A * | 7/1996 | Weber | 411/33 |
| 6,095,817 A * | 8/2000 | Wagner et al. | 433/173 |
| 6,776,617 B2 * | 8/2004 | Lax | 433/221 |
| 7,169,317 B2 * | 1/2007 | Beaty | 216/109 |
| 2004/0038180 A1 | 2/2004 | Mayer et al. | |

FOREIGN PATENT DOCUMENTS

| | | |
|---|---|---|
| EP | 0 434 591 A1 | 6/1991 |
| EP | 0 820 737 A2 | 1/1998 |

* cited by examiner

*Primary Examiner*—Rick K Chang
(74) *Attorney, Agent, or Firm*—Scully, Scott, Murphy & Presser, P.C.

(57) ABSTRACT

A method for manufacturing a one-piece dental implant. The method includes the steps, in any order, of manufacturing an outer body of metal having a cavity and manufacturing an inner body of plastic or composite material having an outer profile. The cavity has an inner profile, and the outer profile of the inner body is complementary to the inner profile of the cavity of the outer body. The inner body includes a core manufactured within the cavity of the outer body. The respective profiles are wavelike rounded in an axial direction of the dental implant and tapering from the crestal end of the outer body to the apical end of the outer body, such as to decrease tension between the inner and the outer bodies and/or such that to provide for an anti-rotation lock between the two bodies.

17 Claims, 2 Drawing Sheets

METHOD FOR MANUFACTURING ONE-PIECE DENTAL DEVICE

This application claims priority to European patent application Serial No. EPA 04011868.9 filed on May 19, 2004.

The invention relates in general to a one-piece dental device and to a method to manufacture the same and in particular to a one-piece dental implants and to a method of manufacturing the same.

BACKGROUND OF THE INVENTION

Dental devices in general and dental implants in particular are made basically of two classes of materials: metals and ceramics.

With regard to metal, several metals are used for forming implants. Each metal has its own characteristic which renders the metal a possible suitable choice for the dental implants. For example, Ti (titanium) or titanium alloy are generally used. Titanium dental implants are relatively light, have high strength, and they have excellent corrosion resistance and bio-compatibility.

Ceramic materials such as zirconia-based, alumina-based and/or sapphire-based ceramics have also been used for manufacturing dental implants or dental devices.

Dental devices, in general, and dental implants, in particular, formed from ceramic materials have the disadvantage that the material is more brittle as shown by a low value for the notched bar impact test. Ceramic materials are also susceptible to uncontrolled internal and external micro-cracks, and therefore they are prone to fail catastrophically. Moreover, artificial ceramic dental devices are rather expensive. However, the ceramic dental devices in general and the visible section of dental implants in particular, have a better aesthetic impact with respect to the metal implant and therefore enjoy a higher acceptance with the dental device bearer.

Furthermore, in some instances, a dental implant which is made of metal only may come into contact with an abutment/crown which is also made of a metal like for instance titanium, titanium alloy, gold or a gold alloy. Alternatively the abutment/crown is made of ceramic such as zirconia-based, alumina-based (for instance in-ceram®) and/or sapphire-based ceramics, or a ceramic glass composite. In the first metal to metal case, saliva or tissue fluid, acting as an electrolyte, may cause a galvanic electric current to flow which in extreme cases may have unpleasant effects for the dental prosthesis bearer. Also the metal, in particular if metals other than titanium are used in contact with a titanium implant, may cause inflammation and irritation of the soft tissue which it contacts.

In view of the above, there is the need for a dental device, in particular a one-piece dental-device, that combines the advantages of metal made dental devices with those of ceramic made dental devices and which, at the same time, is not subject to the above shortcomings entailed by ceramic materials.

Furthermore, in view of the foregoing, there is the particular need for a dental implant, in particular a one-piece dental implant, that combines the advantages of metal made dental implants with those of ceramic made dental implants, which avoids the use of ceramic material.

SUMMARY OF THE INVENTION

The object of the present invention is to provide dental devices such as a one-piece dental implant, a dental prosthesis and the like that are easy to manufacture and have good bio-compatibility, high strength and a good aesthetic impact.

In one preferred embodiment thereof the present invention is directed to a dental device, in particular a dental implant, which comprises an outer body made of metal and an inner body made of a plastic material, wherein the outer metal body is manufactured preferably by metal injection molding (MIM) or Ti Plasma spraying or by lathe processing or the like and the inner body is preferably manufactured from a plastic material by molding, for instance plastic injection molding (PIM), or composite material produced for instance with composite flow molding (CFM) process.

Preferably the metal according to the present invention is titanium, titanium alloy or any other comparable materials. Preferably the plastic material is chosen from a group comprising PEEK (Polyetheretherketon), PPSU (Polyphenylensulfon), PES (Polyethersulfon) or combination or one of the above polymers and a fiber for instance $Al_2O_3$ or $SiO_2$ or $ZrO_2$.

In the case that the present invention is embodied as a one-piece endosseous dental implant it may be comprised of a metal implant part which is to be implanted in a bone tissue, that implant part having a portion defining a metal outer body or a sheath thereof; and a plastic or composite inner body. Both bodies are manufactured by metal injection molding and by plastic injection molding, respectively. Furthermore, the plastic or composite inner body may comprise a core, a collar and a hollow. The inner plastic or composite body extending at the coronal side of the implant preferably forms an abutment. Again, preferably the metal is titanium or a titanium alloy or the like and the plastics is chosen from a group comprising PEEK (Polyetheretherketon), PPSU (Polyphenylensulfon), PES (Polyethersulfon) or combination or one of the above polymers and a fiber for instance zirconia-based, alumina-based and/or sapphire-based ceramic.

Additionally the one-piece endosseous dental implant may be provided with an inner metal sleeve which provides means for fixing to a cap, crown or the like, wherein the inner metal sleeve is located in the hollow of the inner plastic or composite body. Also the inner metal sleeve may be chosen among titanium or a titanium alloy.

Preferably, if the metal outer body is manufactured by metal injection molding it has a rounded inner profile of its cavity which is believed to decrease tension between the inner and the outer bodies. If the outer metal body is lathe processed it is preferred that the inner profile of the cavity of the outer metal body is conically shaped in order to facilitate its manufacturing.

According to one exemplary aspect of the present disclosure, a method for manufacturing a dental device is provided. The method includes manufacturing an outer body of the dental device having a cavity, the outer body made of metal; defining a mold by the cavity and forming an inner profile of the cavity; and injecting a plastic or composite material into the mold for manufacturing an inner body having an outer profile. The inner body includes a core molded within the cavity of the outer body through the mold. A section of the core, which is in contact with the inner profile of the cavity of the outer body, defines the outer profile of the inner body and is complementary to the inner profile of the cavity of the outer body. The inner and outer profiles are wavelike rounded in an axial direction of the dental implant and tapering from a crestal end of the outer body to a apical end of the outer body.

The metal outer body may be manufactured by metal injection molding or mechanically processed by lathe processing milling, drilling or the like. The inner plastic or composite body is formed within a cavity of the metal outer body preferably by plastic injection molding within the cavity.

BRIEF DESCRIPTION OF THE DRAWINGS

The foregoing and other objects, features, and advantages of the invention, as well as presently preferred embodiments thereof, will become more apparent from a reading of the following description, in connection with the accompanying drawings in which.

DESCRIPTION OF THE PREFERRED EMBODIMENTS

Metal injection molding (MIM), plastic injection molding (PIM) and composite flow molding (CFM) are well known technologies in the art of molding. In particular, in the process of plastic injection molding, a plastic material is injected at high temperature and pressure in a mold where it is allowed to cool down and become hardened. Similar to plastic injection molding, a molten polymer (called binder) along with metal powder paste are injected into a mold in the course of metal injection molding. The volume of the part is restricted to small components. The binder material is removed by either solvent extraction or controlled heating to above the volatilization temperatures and the so called green body is sintered.

Metal injection molding consists essentially of the following steps:
  powder manufacture;
  mixing or blending;
  injection molding; and
  preferably sintering.

According to the knowledge of the present inventors, the above described two technologies have never been utilized together in order to form dental implants, in particular one-piece dental implants.

The present invention will be exemplified disclosing an endosseous one-piece dental implant which is envisaged as the currently preferred embodiment thereof. However, it should be understood that the basic principles of the present invention (which includes the combination of metal injection molding and molding techniques for a plastic material) may be applied to other medical/dental devices like for instance dental prosthesis or to prosthetic parts in general. Also, it is believed that the basic principles of the invention are applicable to other non-medical devices.

Figure 1:
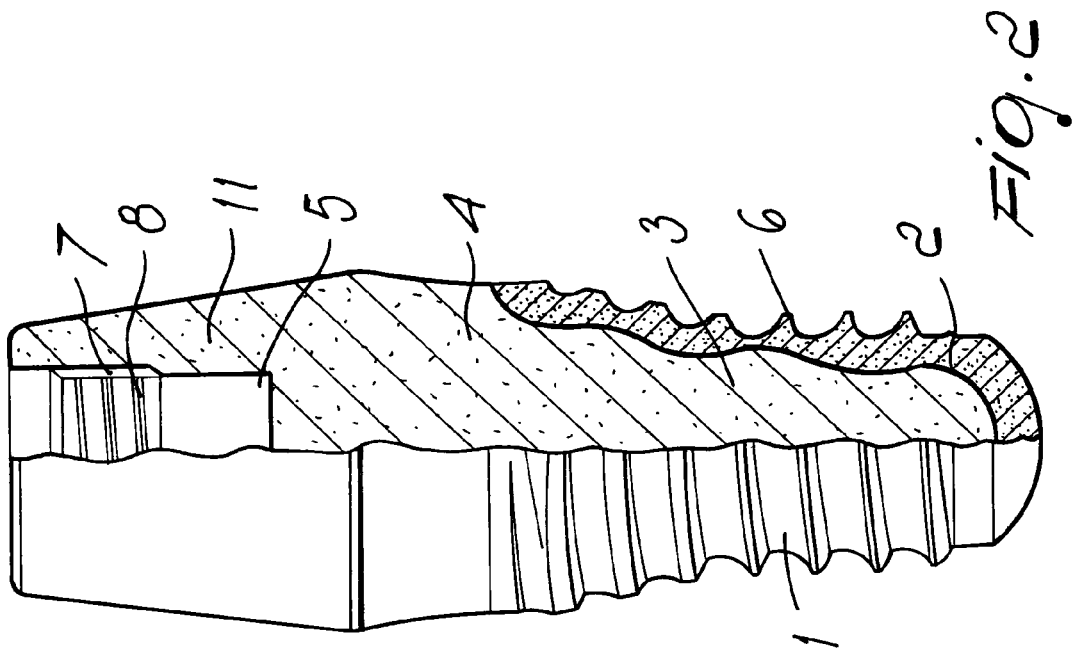
FIG. 1 is a perspective partially cut away view which shows a first embodiment of the invention devised as a one-piece dental device, wherein the outer body is manufactured by metal injection molding and the inner plastic or composite body is manufactured from a plastic material.
Figure 2:
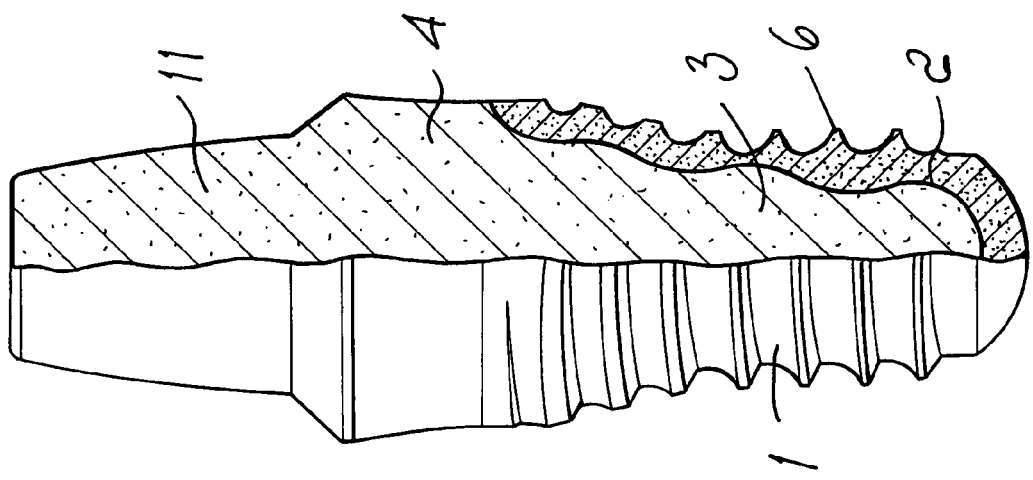
FIG. 2 is a perspective partially cut away view which shows a variation of the one-piece dental device of FIG. 1, wherein the inner plastic or composite body of the dental implant is provided with an inner sleeve.

The endosseous one-piece dental implant of the present invention, as shown in a schematic representation of FIG. 1, comprises a metal-outer body 1 which is to be implanted in bone tissue and an inner plastic body 2 comprising a core 3 forming at a coronal section thereof a collar 4. Coronally of the collar 4 the inner plastic body 2 may comprise an abutment 11. The one-piece dental device of FIG. 2 is formed in a similar manner to the implant of FIG. 1 including in addition an inner sleeve 7, the inner sleeve 7 being located in a hollow 5 defined at the abutment 11 of the inner body 2. Preferably, the inner sleeve 7 is made of a metal like for instance titanium.

As well known in the relevant art, the metal outer body 1 may be preferably provided with an external thread structure 6. Furthermore, the section of the outer body 1 in contact with the bone tissue may be treated to give it a special surface morphology or chemical properties preferably by sandblasting and/or acid-etching (for instance by the SLA—Sandblasted, Large grit, Acid-etched—surface treatment method). Also titanium plasma spraying thereof is intended to be within the scope of the invention. Preferably sandblasting is performed with glass beads or $Al_2O_3$ grits or $TiO_2$ grits. The surface of the implant in contact with the gingival tissue may be advantageously smooth, but other surface treatments to improve soft tissue attachment are possible. In addition, surface modification at the soft tissue and/or bone tissue apposition surface can be done by growth factor adsorption, and/or peptide adsorption, and/or protein adsorption, and/or amino acid adsorption. The SLA-interface may be designed advantageously to follow the outline of the tissue and is not necessarily identical to the interface between the inner body 2 and the outer body 1.

The inner shape/profile of a cavity defined within the metal outer body 1 is complementary to the outer profile of the inner body 2.

Preferably, according to the invention, the inner profile of the cavity of the outer body 1 is a rounded profile to decrease tension between the inner and the outer bodies. This complementary rounded profile is particularly advantageous when the present inner and outer bodies are manufactured by means of plastic injection molding and metal injection molding, respectively.

The metal outer body 1 is made preferably of titanium or a titanium alloy or any other comparable materials. The plastic or composite inner body 2 is preferably a plastic or composite material chosen from a group including PEEK (Polyetheretherketon), PPSU (Polyphenylensulfon), PES (Polyethersulfon) or combination or one of the above polymers and a fiber for instance $Al_2O_3$ or $SiO_2$ or $ZrO_2$.

The plastic or composite inner body 2 comprises the core 3 which lies inside the outer body 1. The outer profile of the core 2 has, as explained, a rounded profile which is complementary to the inner profile of the cavity of the metal outer body 1, such that the rounded profile alleviates the tension between the outer body 1 and the inner body 2. The profile may also advantageously be adapted for locking against relative rotation of the two bodies. Thus, the profile includes an anti-rotation feature.

The collar 4 is, in the implanted state of the dental implant, basically in contact with the soft tissue, such that to avoid direct contact of the metal outer body 1 with the soft tissue.

As shown in FIG. 2 the dental implant may optionally be provided with the inner sleeve 7 which provides for a fixing to a cap, crown etc. (not shown), wherein the inner sleeve 7 is located in the hollow 5 defined at the collar 4 of the inner body 2.

Preferably, the inner sleeve 7 of the FIG. 2 is provided in a known manner with a thread 8 and anti-rotation means (for instance of polygonal, octagonal or any other suitable shape) for fixing the cap, crown etc (not shown). The inner sleeve 7 may be coupled to the inner body 2 by snap coupling, press fitting, adhesive coupling, lock engagement, warm shrinking etc. Also it is conceivable according to the present invention to provide combinations of two or more of snap coupling, press fitting, adhesive coupling, lock engagement and warm shrinking between the sleeve 7 and the inner body 2. Furthermore, the sleeve 7 may also be provided by means of a metal injection molding process if it is made of metal or by an ceramic injection molding (CIM) process if ceramics are used therefore. The vertical length of the hollow 5 may vary according to the length of the thread 8 of the sleeve 7 and the anti-rotation means may be omitted.

Figure 3:
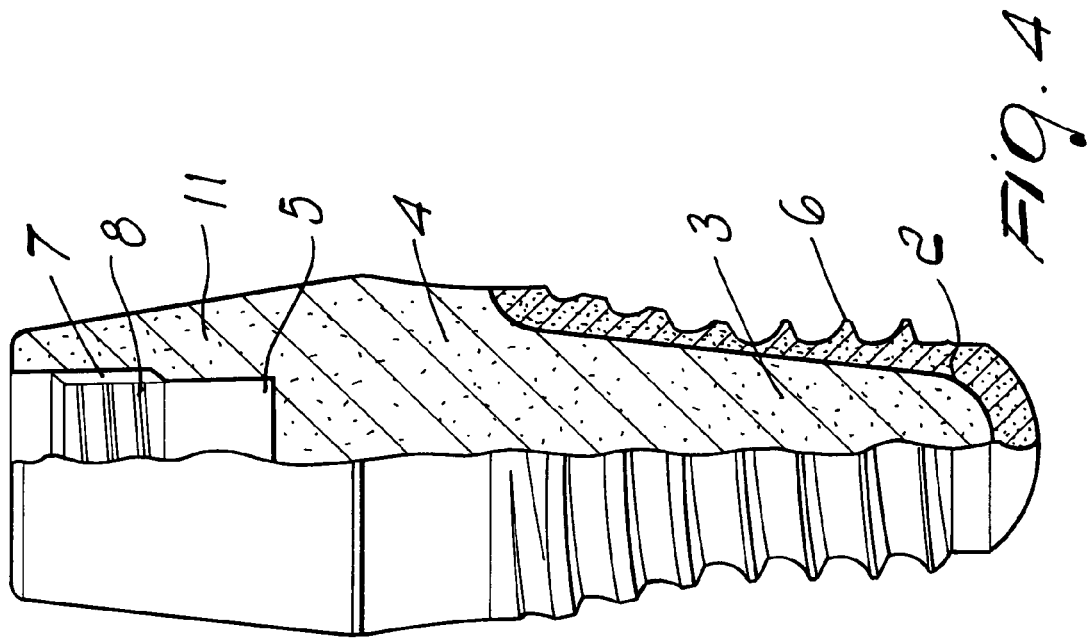
FIG. 3 is a perspective partially cut away view which shows a second embodiment of the invention devised as a one-piece dental device, wherein the outer body is manufactured by lathe processing and the inner body is manufactured from a plastic or composite material.
Figure 4:
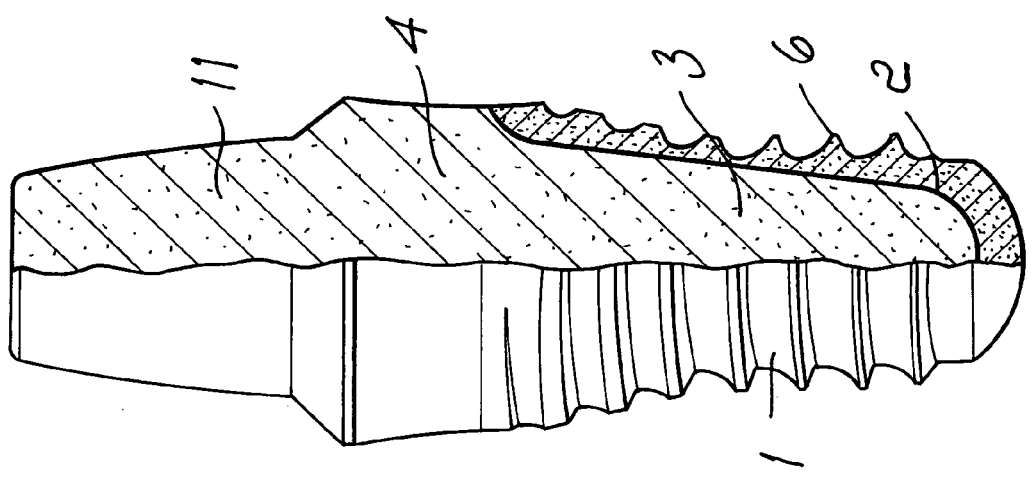
FIG. 4 is a perspective partially cut away view which shows a variation of the one-piece dental device of FIG. 3, wherein the plastic or composite inner body of the dental implant is provided with an inner sleeve.

The one-piece dental implant of FIGS. 3 and 4 is the same as that of FIGS. 1 and 2, respectively, except for the rounded inner profile of the cavity of the metal outer body 1 being replaced by a conical one. Such conical profile of the cavity may result if the inner profile of the cavity of the metal outer body 1 is manufactured by lathe processing, milling, drilling or the like.

The dental implants or dental devices of the present invention, as shown in FIGS. 1 through 4, may be manufactured by means of a method providing for the injection of the plastic material of the plastic inner body 2 into the inner cavity of the metal outer body 1. In this method the inner cavity of the metal outer body 1 is used as a mold and may be advantageously provided at the apical tip thereof with venting orifices. Thus, the inner cavity of the outer metal body 1 functions as a mold for molding the core 3 therein. The collar 4 and the abutment 11, if any, may be molded in a separate cavity (not shown) defining along with the inner cavity of the outer body 1, which may be held as an insert in a molding device, a closed molding chamber.

The metal outer body 1 is preferably molded according to the invention using MIM or mechanically processed by lathe processing, milling, drilling and the like, as already explained.

As the plastic or composite inner body 2 is always molded or provided into the inner cavity of the metal outer body, the two bodies are perfectly shaped and fit perfectly. The preferred method for producing the plastic inner body is plastic injection molding (PIM) while the preferred method for producing the composite inner body is composite flow molding (CFM).

The embodiments described are chosen to provide an illustration of principles of the invention and its practical application to enable thereby the person of ordinary skill in the art to utilize the invention in various embodiments and with various modifications as are suited to the particular use contemplated. In particular, the plastic or composite inner body 2 may be provided by other molding methods, like for instance press molding, extrusion, injection pressing or expanding. Also alternative methods for providing the outer metal body can be implemented. Therefore, the foregoing description is to be considered exemplary, rather than limiting, and the true scope and spirit of the invention is that described in the appended claims.

The disclosures in EPA 04011868.9 from which this application claims priority are incorporated herein by reference.

What is claimed is:

1. A method for manufacturing a dental device, in particular a one-piece dental implant, comprising the following steps:
    manufacturing an outer body of the dental device having a cavity, said outer body made of metal;
    defining a mold by said cavity and forming an inner profile of the cavity; and
    injecting a plastic or composite material into said mold for manufacturing an inner body having an outer profile, wherein the inner body comprises a core molded within the cavity of the outer body through said mold, a section of said core which is in contact with said inner profile of said cavity of said outer body defining said outer profile of said inner body and being complementary to said inner profile of said cavity of said outer body,
    wherein the inner and outer profiles are wavelike rounded in an axial direction of the dental implant and tapering from a crestal end of the outer body to a apical end of the outer body, thereby decreasing tension between the inner and the outer bodies and/or providing an anti-rotation lock between the two bodies.

2. The method of claim 1, wherein the inner body further comprises a collar coronally of the core and an abutment coronally of the collar, and the method further comprising a step of manufacturing the collar and the abutment simultaneously with manufacturing the core and with the same material as the core.

3. The method of claim 1, wherein the dental implant further includes an inner sleeve within a hollow of the inner body, the inner sleeve being adapted for providing fixing means to a cap, a crown or the like, and the method further comprising a step of fixing the inner sleeve to the hollow of the inner body by one or more of snap coupling, press fitting, adhesive coupling, lock engagement and warm shrinking.

4. The method of claim 3, wherein the inner sleeve is provided by a step of a metal injection molding.

5. The method of claim 1, wherein the outer body is provided by metal injection molding or by lathe processing, milling, drilling and the like, and the inner body is provided by plastic injection molding or composite flow molding within the cavity of the outer body.

6. The method of claim 1, wherein the metal is titanium or a titanium alloy, wherein the plastic material is selected from the group consisting of PEEK (Polyetheretherketone), PPSU (Polyphenylensulfone), PES (Polyethersulfone) or combinations thereof; or wherein the composite material is one of said polymers and a fiber including $Al_2O_3$ or $SiO_2$ or $ZrO_2$.

7. The method of claim 1, further including a step of forming the inner profile of the cavity of the outer body complementary to outer profile of the inner body, and wherein the respective profiles are rounded, thereby decreasing tension between the inner and the outer bodies and/or providing an anti-rotation lock between the two bodies.

8. The method of claim 1, wherein the respective profiles are conical.

9. The method of claim 1, further comprising a step of topographically or chemically modifying the implant surface by sandblasting, acid-etching or combination thereof, and/or plasma spraying, and/or growth factor adsorption, and/or peptide adsorption, and/or protein adsorption, and/or amino acid adsorption, and wherein the modification of the implant surface is carried out at a soft tissue and/or bone tissue apposition surface.

10. A method for manufacturing a dental device, in particular a one-piece dental implant, comprising the following steps:
    manufacturing an outer body of the dental device having a cavity, said outer body made of metal;
    defining a mold by said cavity and forming an inner profile of the cavity; and
    injecting a plastic or composite material into said mold for manufacturing an inner body having an outer profile, wherein the inner body comprises a core molded within the cavity of the outer body through said mold, a section of said cavity of said outer body which is in contact with said core of said inner body defining said inner profile of said cavity of said outer body and being complementary to said outer profile of said inner body, and wherein the inner and outer profiles are wavelike rounded in an axial direction of the dental implant and tapering from a crestal end of the outer body to a apical end of the outer body, thereby decreasing tension between the inner and the outer bodies and/or providing an anti-rotation lock between the two bodies.

11. The method of claim 10, wherein the inner body further comprises a collar coronally of the core and an abutment coronally of the collar, and the method further comprising a step of manufacturing the collar and the abutment simultaneously with manufacturing the core and with the same material as the core.

12. The method of claim 10, wherein the dental implant further includes an inner sleeve within a hollow of the inner body, the inner sleeve being adapted for providing fixing means to a cap, a crown or the like, and the method further comprising a step of fixing the inner sleeve to the hollow of the inner body by one or more of snap coupling, press fitting, adhesive coupling, lock engagement and warm shrinking.

13. The method of claim 12, wherein the inner sleeve is provided by a step of a metal injection molding.

14. The method of claim 10, wherein the outer body is provided by metal injection molding or by lathe processing, milling, drilling and the like, and the inner body is provided by plastic injection molding or composite flow molding within the cavity of the outer body.

15. The method of claim 10, wherein the metal is titanium or a titanium alloy, wherein the plastic material is selected from the group consisting of PEEK (Polyetheretherketone), PPSU (Polyphenylensulfone), PES (Polyethersulfone) or combinations thereof; or wherein the composite material is one of said polymers and a fiber including $Al_2O_3$ or $SiO_2$ or $ZrO_2$.

16. The method of claim 10, further comprising a step of topographically or chemically modifying the implant surface by sandblasting, acid-etching or combination thereof, and/or plasma spraying, and/or growth factor adsorption, and/or peptide adsorption, and/or protein adsorption, and/or amino acid adsorption, and wherein the modification of the implant surface is carried out at a soft tissue and/or bone tissue apposition surface.

17. A method for manufacturing a one-piece dental implant, comprising the following steps:

manufacturing an outer body of the dental device having a cavity, said outer body made of metal;

defining a mold by said cavity and forming an inner profile of the cavity; and injecting a plastic or composite material into said mold for manufacturing an inner body having an outer profile;

wherein the inner body comprises a core molded within the cavity of the outer body through said mold, a section of said core which is in contact with said inner profile of said cavity of said outer body defining said outer profile of said inner body and being complementary to said inner profile of said cavity of said outer body, and wherein the inner body further comprises a collar coronally of the core and an abutment coronally of the collar, manufactured simultaneously with manufacturing the core and with the same material as the core;

wherein said inner and outer profiles are wavelike rounded in an axial direction of the dental implant and tapering from a crestal end of the outer body to a apical end of the outer body, thereby decreasing tension between the inner and the outer bodies and/or providing an anti-rotation lock between the two bodies.

* * * * *